(12) United States Patent
He et al.

(10) Patent No.: US 12,385,863 B2
(45) Date of Patent: Aug. 12, 2025

(54) METHOD FOR EVALUATING THERMAL PROTECTION DURATION OF FABRIC

(71) Applicant: SOOCHOW UNIVERSITY, Suzhou (CN)

(72) Inventors: Jiazhen He, Suzhou (CN); Yehu Lu, Suzhou (CN); Jun Li, Suzhou (CN)

(73) Assignee: SOOCHOW UNIVERSITY, Suzhou (CN)

(*) Notice: Subject to any disclaimer, the term of this patent is extended or adjusted under 35 U.S.C. 154(b) by 811 days.

(21) Appl. No.: 17/763,859

(22) PCT Filed: Mar. 5, 2021

(86) PCT No.: PCT/CN2021/079194
§ 371 (c)(1),
(2) Date: Mar. 25, 2022

(87) PCT Pub. No.: WO2021/248943
PCT Pub. Date: Dec. 16, 2021

(65) Prior Publication Data
US 2022/0317075 A1    Oct. 6, 2022

(30) Foreign Application Priority Data

Jun. 7, 2020 (CN) .......................... 202010509586.X

(51) Int. Cl.
*G01N 25/20* (2006.01)
*G01N 33/36* (2006.01)

(52) U.S. Cl.
CPC ........... *G01N 25/20* (2013.01); *G01N 33/367* (2013.01)

(58) Field of Classification Search
CPC .............................. G01N 25/20; G01N 33/367
See application file for complete search history.

(56) References Cited

U.S. PATENT DOCUMENTS 10,183,465 B1    1/2019  Bowman et al.
2014/0259331 A1  9/2014  Maples et al.

FOREIGN PATENT DOCUMENTS

CN    105203588 A  * 12/2015
CN    105301043 B  *  4/2018
(Continued)

OTHER PUBLICATIONS

Mengying Zhang et al. "Influence factors and evaluation methods of stored thermal energy in firefighters protective clothing" Journal of Textile Research, vol. 37, No. 6, pp. 171-176.

*Primary Examiner* — Mirellys Jagan
(74) *Attorney, Agent, or Firm* — SZDC Law PC

(57) ABSTRACT

The invention discloses a method for evaluating a thermal protection duration of a fabric. A persistent thermal exposure duration for skin to reach a second-degree burn when heat storage release of a fabric is not considered and a corresponding first safe cooling duration are determined, a minimum thermal exposure duration for skin to reach a second-degree burn when heat storage release of a fabric is completely considered and a corresponding second safe cooling duration are determined, and a plurality of safe thermal exposure durations between the minimum and persistent thermal exposure durations and a plurality of third safe cooling durations are determined. The plurality of thermal exposure durations are used as x data and the plurality of cooling durations are used as y data to obtain a safe duration curve. The curve, x-axis, and y-axis further form a closed area to obtain a safe duration zone of the fabric.

10 Claims, 1 Drawing Sheet

(56) References Cited

FOREIGN PATENT DOCUMENTS

| CN | 108511060 | A |   | 9/2018  |             |
|----|-----------|---|---|---------|-------------|
| CN | 109374673 | A | * | 2/2019  |             |
| CN | 110501376 | A | * | 11/2019 |             |
| CN | 111521637 | A |   | 8/2020  |             |
| CN | 111537558 | A | * | 8/2020  | G01N 25/20  |

* cited by examiner

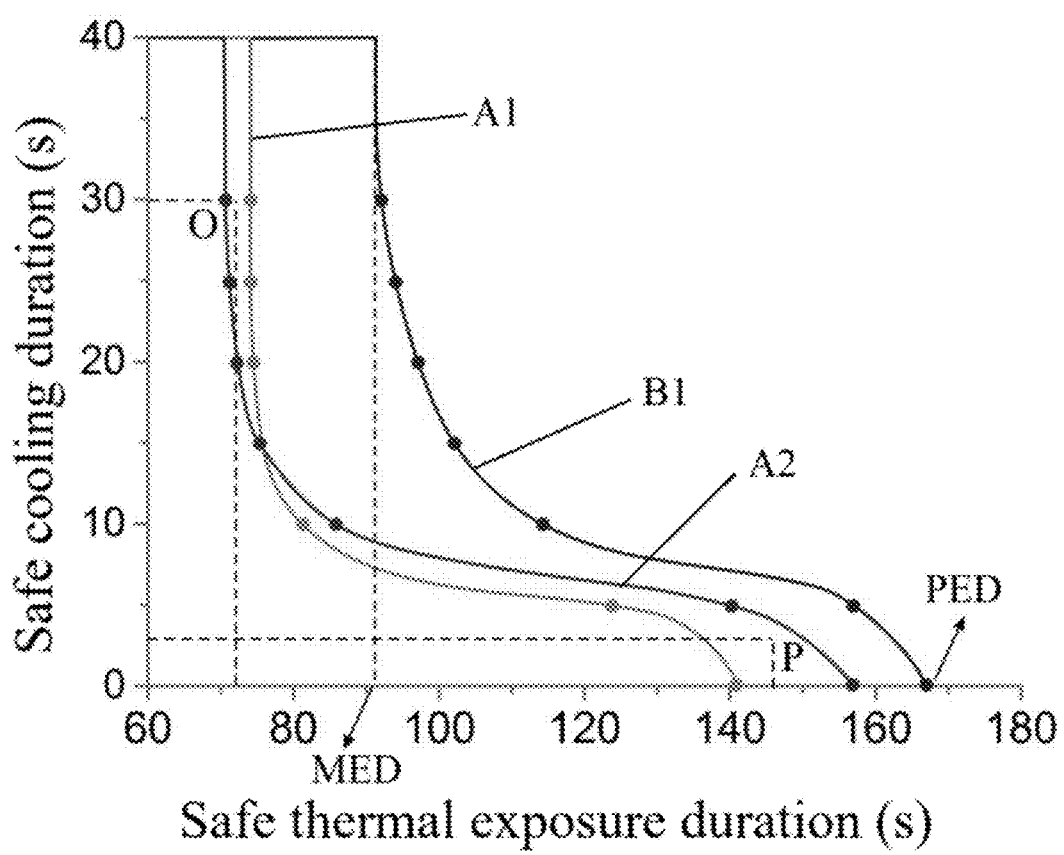

METHOD FOR EVALUATING THERMAL PROTECTION DURATION OF FABRIC

CROSS-REFERENCE TO RELATED APPLICATION

This application is the National Stage Application of PCT/CN2021/079194, filed on Mar. 5, 2021, which claims priority to Chinese patent application No. 202010509586.X, entitled "METHOD FOR EVALUATING THERMAL PROTECTION DURATION OF FABRIC," filed on Jun. 7, 2020, the disclosure of which is hereby incorporated by reference in its entirety.

FIELD OF THE INVENTION

The present invention relates to the field of thermal protection technologies, and more particularly to a method for evaluating a thermal protection duration of a fabric.

DESCRIPTION OF THE RELATED ART

Thermal protective performance test methods and standards are the basis for the development of high-performance protective clothing and equipment. At present, many countries have put forward legislative requirements for the performance of thermal protective materials and products, and evaluation methods and test equipment for the thermal protective performance of fabrics are being developed and improved. The development of methods for evaluating thermal protective performance of fabrics is mainly divided into heat transfer performance testing in the early stage and comprehensive thermal protective performance testing based on skin burn prediction in the later stage with 2018 as the node. Specifically, before 2018, the testing of heat transfer performance of fabrics in a thermal exposure stage was mainly referred to test standards ASTM D4108-87 and ASTM F1939-99a, which have been abolished and replaced with ASTM F2700-08 and ASTM F1939-08. However, in current ASTM F2700-08 and ASTM F1939-08, only an amount of heat transfer through a fabric during the exposure of the fabric to a heat source is acquired. Therefore, it is only possible to assess the insulative-protective performance of a fabric on heat transfer from a thermally hazardous environment in a thermal exposure stage. The harm of continuous heat transfer to skin caused by the discharge of heat storage from the fabric after the fabric is removed from the heat source is ignored. Therefore, the standards cannot be used to predict skin burns.

To comprehensively assess the thermal insulative-protective performance of fabrics in a thermal exposure stage and the thermal hazardous performance by heat release in a cooling stage, three test standards ASTM F2702-08, ASTM F2703-08, and ASTM F2731-11 that can predict skin burns were reformulated after 2018 by the American Society for Testing and Materials. These standards specify that sensor data continue to be acquired after thermal exposure of a fabric ends and are used for assessing a comprehensive effect of thermal protective and thermal hazardous performance of the fabric throughout thermal exposure and thermal cooling, thereby implementing skin burn prediction. In the three test methods, a complete process of heat transfer between clothing and human body is considered to fully evaluate both the thermal protective and thermal hazardous performance of thermal protective clothing for human skin.

However, there are still certain defects in the existing methods for testing and evaluating the thermal protective performance of fabrics. The standards for testing the heat transfer performance of fabrics (ASTM F2700-08 and ASTM F1939-08) ignore the hazards of heat storage discharge from a fabric to skin after thermal exposure ends and as a result cannot assess skin burns. The standards for testing the comprehensive thermal protective performance of fabrics (ASTM F2702-08, ASTM F2703-08, and ASTM F2731-11) have completely considered the thermal insulative-protective performance of a fabric in a thermal exposure stage and the thermal hazardous performance caused by heat storage discharge in a cooling stage. However, the evaluation index in the standards is still determined by a "single thermal exposure duration value". The value only characterizes a "minimum thermal exposure duration (MED)" when skin covered by a fabric just reaches a second-degree burn. It is found that during actual use the series of methods based on the test standards ASTM F2702-08, ASTM F2703-08, and ASTM F2731-11 still have several limitations as follows.

(1) Lack of information on a true skin burn time. The MED in essence only provides information about a thermal exposure duration of a fabric when skin reaches a second-degree burn but does not address a true second-degree burn protection duration value.

(2) The method may fail in practical applications. In a possible case during actual operations, different fabrics may have the same MED, but the heat release durations of the fabrics required to reach a second-degree burn are different. For this case, it is very difficult to use the current test standards to further distinguish between the real thermal protective performance of these fabrics.

(3) It is difficult to describe the "variable thermal protection duration" property of a fabric. In the study, it is found that the thermal protective performance of a fabric system A is better than that of a fabric system B when the heat release of a fabric is not considered, but the thermal protective performance of A is lower than that of B when the heat release of a fabric is considered. This indicates that under different test conditions, a fabric can provide "variable thermal protection duration" for skin, while a conventional "single thermal protection duration" theory for a fabric is not applicable to study the thermal protection under complex and variable conditions.

Therefore, it is necessary to explore differences in the thermal protective performance of a fabric under different conditions, and at the same time reestablish an appropriate and accurate method for evaluating the thermal protective performance of a fabric to fully exhibit the thermal protection provided by a fabric for human skin under different conditions.

SUMMARY OF THE INVENTION

To overcome deficiencies in the prior art, embodiments of the present invention provide a method for evaluating a thermal protection duration of a fabric, which is used for reestablishing an appropriate and accurate method for evaluating the thermal protective performance of a fabric to fully exhibit the thermal protection provided by a fabric for human skin under different conditions.

Embodiments of the present application disclose a method for evaluating a thermal protection duration of a fabric, including the following steps:

exposing a front surface of a first fabric to a simulated heat source for to seconds, and continuously acquiring a first heat flux absorbed by a skin simulant sensor on a rear surface of the first fabric within the to seconds;

obtaining a persistent thermal exposure duration according to the first heat flux, a human skin heat transfer model, and a burn integral model, where the persistent thermal exposure duration represents a maximum duration of allowable continuous thermal exposure of the first fabric for human skin to reach a second-degree burn; specifically, the persistent thermal exposure duration is the maximum duration of allowable continuous thermal exposure of the first fabric for human skin to just reach a second-degree burn when only heat transfer of the first fabric during a thermal exposure stage is considered and heat storage release from the first fabric in a cooling stage is not considered; when the persistent thermal exposure duration of the first fabric exceeds the maximum duration, even if a heat release duration of the first fabric to skin in the cooling stage is 0 second, human skin reaches a second-degree burn;

obtaining a first safe cooling duration corresponding to the persistent thermal exposure duration according to the persistent thermal exposure duration;

exposing a front surface of a second fabric to the simulated heat source for $t_1$ seconds, subsequently making the second fabric leave the simulated heat source to perform cooling, and continuously acquiring a second heat flux absorbed by a skin simulant sensor on a rear surface of the second fabric during the $t_1$ seconds of thermal exposure and a preset duration of a cooling stage, where the second fabric is the same as the first fabric, and $t_1 < t_0$;

obtaining a minimum thermal exposure duration according to the second heat flux, the human skin heat transfer model, and the burn integral model, where the minimum thermal exposure duration represents a minimum duration of required continuous thermal exposure of the second fabric for human skin to reach a second-degree burn; specifically, the minimum thermal exposure duration is the minimum duration of the required continuous thermal exposure of the second fabric for human skin to just reach a second-degree burn when both heat transfer of the second fabric in a thermal exposure stage is considered and heat release of the second fabric in a cooling stage is fully considered; when the persistent thermal exposure duration of the second fabric does not reach the minimum duration, even if a heat release duration of the first fabric to skin in the cooling stage is infinitely long, human skin does not reach a second-degree burn;

obtaining a second safe cooling duration corresponding to the minimum thermal exposure duration according to the minimum thermal exposure duration;

separately exposing front surfaces of a plurality of third fabrics to the simulated heat source for $t_{trial}$ seconds, subsequently removing the third fabrics from the simulated heat source to perform cooling, continuously acquiring a third heat flux absorbed by skin simulant sensors on rear surfaces of third fabrics during the $t_{trial}$ seconds of thermal exposure and the preset duration of the cooling stage, where the minimum thermal exposure duration$<t_{trial}<$the persistent thermal exposure duration, the plurality of third fabrics have different $t_{trial}$, and the third fabrics are the same as the first fabric;

obtaining a third safe cooling duration corresponding to the safe thermal exposure duration of $t_{trial}$ according to the third heat flux, the skin heat transfer model, and the burn integral model; and obtaining a safe duration curve according to the persistent thermal exposure duration, the first safe cooling duration corresponding to the persistent thermal exposure duration, the minimum thermal exposure duration, the second safe cooling duration corresponding to the minimum thermal exposure duration, a plurality of safe thermal exposure durations, and a plurality of third safe cooling durations corresponding to the plurality of safe thermal exposure durations.

Specifically, the skin heat transfer model is:

$$\rho c \frac{\partial T(x, t)}{\partial t} = k \frac{\partial^2 T(x, t)}{\partial x^2},$$

where $\rho$, c, and k are respectively a density, a specific heat capacity, and a thermal conductivity of skin, and $T(x, t)$ is a temperature of a skin layer at a depth of x at a moment t.

Specifically, the burn integral model is:

$$\Omega = \int_0^t P \exp\left(\frac{-\Delta E}{RT}\right) dt,$$

where $\Omega$ is burn injury parameter and is dimensionless; $\Delta E$ and P are respectively activation energy of skin and a frequency factor; R is a universal gas constant; T is an absolute temperature of skin; t is a duration for which the skin temperature T is greater than 44° C.; and when $\Omega$ is greater than or equal to 1.0, skin reaches a second-degree burn.

Specifically, a method for obtaining the persistent thermal exposure duration and the first safe cooling duration includes the following steps:

predicting temperature fields at depths inside skin according to the skin heat transfer model of a human body and using the first heat flux as a boundary condition of the skin heat transfer model; and retrieving a temperature change at an epidermis/dermis interface of skin in the temperature fields, and calculating, according to the burn integral model of a human body, a duration when a human skin second-degree burn threshold $\Omega$ is equal to 1.0, the duration is the persistent thermal exposure duration, and because the first fabric has made human skin reach a second-degree burn in a persistent thermal exposure stage, the first safe cooling duration is 0, that is, when a thermal exposure duration of the first fabric reaches the persistent thermal exposure duration, even if heat release of heat storage in the fabric to skin in the cooling stage is not considered, heat absorbed by human skin in the thermal exposure stage is sufficient to cause a second-degree burn.

Specifically, a method for obtaining the minimum thermal exposure duration and the second safe cooling duration includes the following steps:

predicting temperature fields at depths inside skin according to the skin heat transfer model and using the second heat flux as a boundary condition of the skin heat transfer model; and retrieving a temperature change at an epidermis/dermis interface of skin in the temperature fields, and calculating, according to the burn integral model, a duration when a human skin second-degree burn threshold $\Omega$ is just equal to 1.0, where the duration is a total duration of a required thermal exposure duration and a required cooling duration of the second fabric for human skin to just reach a second-degree burn, a thermal exposure duration corresponding to the threshold is the minimum thermal exposure duration of the second fabric, and a difference between the total duration and the minimum thermal exposure duration is the second safe cooling duration.

Specifically, a method for obtaining the third safe cooling duration includes the following steps:

predicting temperature fields at depths inside skin according to the skin heat transfer model and using the third heat flux as a boundary condition of the skin heat transfer model; and retrieving a temperature change at an epidermis/dermis interface of skin in the temperature fields, and calculating, according to the burn integral model, a duration when a human skin second-degree burn threshold Ω is equal to 1.0, where the duration is a total duration of a required thermal exposure duration and a required cooling duration of the third fabric for human skin to reach a second-degree burn, and a difference between the total duration and corresponding $t_{trial}$ is the third safe cooling duration.

Specifically, a method for acquiring the first heat flux includes the following steps:

continuously exposing the first fabric in the simulated heat source for $t_0$ seconds, making the front surface of the first fabric face the simulated heat source, and placing the skin simulant sensor on the rear surface of the first fabric to continuously acquire heat for $t_0$ seconds to obtain the first heat flux; and Specifically, a method for acquiring the second heat flux includes the following steps:

continuously exposing the second fabric in the simulated heat source for $t_1$ seconds, making the front surface of the second fabric face the simulated heat source, and placing the skin simulant sensor on the rear surface of the second fabric to continuously acquire heat that transfers through the second fabric within $t_1$ seconds; and after thermal exposure of the second fabric ends, removing the second fabric from the simulated heat source to perform cooling, continuously applying a pressure of 13.8±0.7 kPa to the front surface of the second fabric, to make the rear surface of the second fabric tightly contact the skin simulant sensor to simulate a process that a fabric is compressed to quickly release heat storage to skin, and continuously acquiring a heat flux through the rear surface of the second fabric by using the skin simulant sensor within 60 seconds after the cooling stage is started, where the heat flux is continuously acquired by the second fabric in a thermal exposure stage and the cooling stage is the second heat flux.

Specifically, a method for acquiring the third heat flux includes the following steps:

continuously exposing the third fabric in the simulated heat source for the $t_{trial}$ seconds, making the front surface of the third fabric face the simulated heat source, and placing the skin simulation sensor on the rear surface of the third fabric to continuously acquire heat that passes through the third fabric within the $t_{trial}$ seconds; and after thermal exposure of the third fabric ends, removing the third fabric from the simulated heat source to perform cooling, continuously applying a pressure of 13.8±0.7 kPa to the front surface of the third fabric, to make the rear surface of the third fabric tightly contact the skin simulation sensor to simulate a process in which a fabric is pressed to quickly release stored heat to skin, and continuously acquiring a heat flux on the rear surface of the third fabric by using the skin simulation sensor within 60 seconds after the cooling stage is started, where the heat flux is continuously acquired by the third fabric in a thermal exposure stage and the cooling stage is the third heat flux.

Specifically, the simulated heat source has a heat flux of 8.5±0.5 kW/m².

Specifically, the skin simulation sensor is a water-cooled heat flux sensor.

Specifically, the step of "obtaining a safe duration curve according to the persistent thermal exposure duration, the first safe cooling duration corresponding to the persistent thermal exposure duration, the minimum thermal exposure duration, the second safe cooling duration corresponding to the minimum thermal exposure duration, a plurality of safe thermal exposure durations, and a plurality of third safe cooling durations corresponding to the plurality of safe thermal exposure durations" includes: obtaining the safe duration curve by using the persistent thermal exposure duration, the minimum thermal exposure duration, and the plurality of safe thermal exposure durations as x-coordinate data and using the respectively corresponding first safe cooling duration, second safe cooling duration, and the plurality of third safe cooling durations as y-coordinate data.

Specifically, a close area formed by a boundary being the safe duration curve, an x-axis, and a y-axis is defined as a safe duration zone of the fabric.

The present invention has the following beneficial effects:

(1) The defect of the lack of information on "cooling duration" in existing integrated methods for testing the thermal protective performance of fabrics is remedied. The existing measurement standards (ASTM F2702-08, ASTM F2703-08, and ASTM F2731-11) only measure a minimum thermal exposure duration when skin just reaches a second-degree burn but do not involve a heat release duration of a fabric to cause a skin burn, that is, cooling duration information. The cooling duration is related to an amount of heat released from a fabric to skin and is therefore related to a skin burn. In the method provided in the present invention, the "safe duration zone" includes a safe thermal exposure duration and a safe cooling duration, so that the defect of missing information in the existing methods is remedied.

(2) Thermal protection duration information of a fabric is comprehensively provided. In existing methods for testing and evaluating the thermal protective performance of a fabric, a "single thermal exposure duration" is used for description. In a real situation, a duration for which an operator is exposed to a heat source is not a fixed value but depends on a thermal hazardous environment and other operating conditions. Different thermal exposure durations affect an amount of heat transfer through a fabric during a thermal exposure stage and also affect an amount of heat release from the fabric to skin during a cooling stage, further causing a corresponding change in a protection duration for human skin. That is, different thermal exposure durations correspond to different thermal protection duration values. The thermal protective performance under a "variable thermal exposure duration" cannot be evaluated by using the existing methods. In the method provided in the present invention, information about a safe thermal exposure duration and a safe thermal cooling duration of a fabric for preventing human skin from burns are comprehensively exhibited in the form of a two-dimensional plane view to form a "safe duration zone" to comprehensively evaluate a thermal protection duration of a fabric, so that an end user such as a firefighter can fully grasp a safe operation duration range for preventing skin from burns.

To make the foregoing and other objectives, features, and advantages of the present invention clearer and more comprehensible, a detailed description is provided below with reference to preferred embodiments in conjunction with the accompanying drawings.

BRIEF DESCRIPTION OF THE DRAWINGS

For clearer descriptions of the technical solutions in the embodiments of the present invention or the prior art, the following briefly introduces the accompanying drawings required for describing the embodiments of the prior art. Apparently, the accompanying drawings in the following description show merely some embodiments of the present invention, and persons of ordinary skill in the art may still derive other drawings from these accompanying drawings without any creative efforts.

FIG. 1 is a schematic diagram of a wearing safe duration area of a test sample of a fabric according to an embodiment of the present invention.

DETAILED DESCRIPTION OF THE PREFERRED EMBODIMENTS

The following clearly and completely describes the technical solutions in embodiments of the present invention with reference to the accompanying drawings in embodiments of the present invention. Apparently, the described embodiments are merely some rather than all of the embodiments of the present invention. All other embodiments obtained by persons of ordinary skill in the art based on the embodiments of the present invention without creative efforts shall fall within the protection scope of the present invention.

In this embodiment, protection durations of three multilayer thermal protective fabrics numbered A1, A2, and B1 are comprehensively evaluated. Each of three multilayer fabric systems is formed by an outer layer, a waterproof breathable moisture barrier, and a thermal liner. The thicknesses of the three fabric systems are respectively 2.48 mm for A1, 2.59 mm for A2, and 3.14 mm for B1. A stored energy tester for a fabric is used for measurement in this embodiment. The test instrument conforms to ASTM F2731-11. Evaluation steps are as follows:

Step 1: A persistent thermal exposure duration (PED) for skin to reach a second-degree burn when heat release of a fabric is not considered. Results are shown in the following Table 1. The persistent thermal exposure duration is specifically obtained by using the following substeps:

Substep 1-1: Set a thermal exposure level to 8.5±0.5 kW/m², that is, expose a fabric (that is, a first fabric) to a simulated heat source with a heat flux of 8.5±0.5 kW/m², make a front surface of the fabric face the heat source, and place a water-cooled sensor simulating skin on a rear surface of the fabric to acquire a heat flux passing through the fabric, that is, simulate acquisition of a heat flux absorbed by skin.

Substep 1-2: Continuously expose the fabric to the simulated heat source, set a thermal exposure duration to $t_0$, and continuously acquire a heat flux of the water-cooled sensor;

Substep 1-3: Predict temperature fields at depths inside skin (including a cuticular layer, a dermal layer, and subcutaneous tissue) according to the Fourier partial differential equation, and as shown in Formula 1, use the heat flux of the sensor obtained in Substep 1-2 as a boundary condition of a skin heat transfer model.

$$\rho c \frac{\partial T(x, t)}{\partial t} = k \frac{\partial^2 T(x, t)}{\partial x^2} \qquad \text{(Formula 1)}.$$

In the formula, ρ, c, and k are respectively a density, a specific heat capacity, and a thermal conductivity of skin, and T(x, t) is a temperature of a skin layer at a depth of x at a moment t.

Substep 1-4: Retrieve a temperature change at an epidermis/dermis interface of skin in the temperature fields, and predict a skin burn by using the Henriques burn integral model (as shown in Formula 2):

$$\Omega = \int_0^t P \exp\left(\frac{-\Delta E}{RT}\right) dt \qquad \text{(Formula 2)}.$$

In the formula, Ω is a burn injury parameter and is dimensionless; ΔE and P are respectively activation energy of skin and a frequency factor; R is a universal gas constant; T is an absolute temperature of skin; t is a duration for which a skin temperature T is greater than 44° C. When the value of Ω at the epidermis/dermis interface satisfies 0.53≤Ω<1.0, the skin reaches a first-degree burn; when Ω≥1.0, the skin reaches a second-degree burn. A duration when a second-degree skin burn threshold Ω=1.0 is calculated. The duration is the persistent thermal exposure duration causing a second-degree burn;

TABLE 1

Persistent thermal exposure durations (PED) of test samples of fabrics

| Fabric system number | A1 | A2 | B1 |
|---|---|---|---|
| PED (seconds) | 141.6 | 157.4 | 167.4 |

Step 2: Measure a minimum thermal exposure duration (MED) for skin to reach a second-degree burn when heat release of a fabric is fully considered. MED represents a thermal exposure duration for skin to just reach a second-degree burn under a condition that an amount of heat transfer passing through the fabric in a thermal exposure stage and an amount of heat release from the fabric to skin in a cooling stage are comprehensively considered. Results are shown in Table 2. The MED is specifically obtained by using the following substeps:

Substep 2-1: Set a thermal exposure level to 8.5±0.5 kW/m², take a test sample of a new fabric (that is, a second fabric), make a front surface of the fabric face the heat source, and place a water-cooled sensor simulating skin on a rear surface of the fabric to acquire a heat flux passing through the fabric, to simulate acquisition of a heat flux absorbed by skin.

Substep 2-2: Continuously expose the fabric to the simulated heat source, set a thermal exposure duration $t_1$ to PED/2 (PED is obtained in Step 1), and continuously acquire a heat flux of the water-cooled sensor; after thermal exposure ends, make the fabric leave the heat source, apply a pressure of 13.8±0.7 kPa to the front surface of the fabric, and keep applying the pressure to the fabric, and after cooling starts, continuously acquire data of the water-cooled sensor in the cooling stage, where a data acquisition duration of the cooling stage is 60 seconds.

Substep 2-3: Predict temperature fields at depths inside skin according to Formula 1, and use the heat flux of the sensor in the thermal exposure stage and the cooling stage obtained in Substep 2-2 as a boundary condition of the skin heat transfer model.

Substep 2-4: Determine, according to the Henriques burn integral model in Formula 2, whether skin just reaches a second-degree burn, that is, determine whether the second-degree skin burn threshold $\Omega$ is just equal to 1.0. If $\Omega$ is equal to 1.0, a thermal exposure duration corresponding to the threshold is denoted as MED.

Substep 2-5: If skin does not burn in Substep 2-4 (that is, the second-degree skin burn threshold $\Omega$ is less than 1.0), change the test sample, and extend the thermal exposure duration $t_1$ to make $t_1$ satisfy PED/2<$t_1$<PED. An iterative experiment is used to repeat substeps 2-1 to 2-4 until skin just reaches a second-degree burn. In this case, the second-degree skin burn threshold $\Omega$ is equal to 1.0, and a thermal exposure duration corresponding to this case is denoted as MED.

Substep 2-6: If skin burns in Substep 2-4 (that is, the second-degree skin burn threshold $\Omega$ is greater than 1.0), change the test sample, and shorten the thermal exposure duration $t_1$ to make it satisfy $t_1$<PED/2. The iterative experiment is used to repeat substeps 2-1 to 2-4 until skin just reaches a second-degree burn. In this case, the second-degree skin burn threshold $\Omega$ is equal to 1.0, and a thermal exposure duration corresponding to this case is denoted as MED.

TABLE 2

Minimum thermal exposure durations (MED) of test samples of fabrics

| Fabric system number | A1 | A2 | B1 |
|---|---|---|---|
| MED (seconds) | 74.0 | 70.3 | 91.3 |

As can be seen from the results of Table 1 and Table 2, when heat release of a fabric is not considered, measurement results of thermal exposure durations of the test samples are $PED_{B1}$>$PED_{A2}$>$PED_{A1}$. However, after heat release of a fabric in the cooling stage is considered, the measurement results of the thermal exposure durations of the test samples are $MED_{B1}$>$MED_{A1}$>$MED_{A2}$.

Step 3: Determine a plurality of discrete safe thermal exposure durations and safe cooling durations within a wearing safe duration area. In the wearing safe duration area defined in the present invention, MED and PED are only critical safe thermal exposure duration values. PED is a maximum critical value of the safe thermal exposure duration. According to a specific value of each safe thermal exposure duration, the following cases of a safe cooling duration are included:

(1) When a safe thermal exposure duration $t_{exp}$<MED, skin does not reach a second-degree burn regardless of a cooling duration. In this case, a theoretical safe cooling duration $t_{co1}$ of the fabric may be infinitely long, that is, $t_{co1}$=+∞.

(2) When a safe thermal exposure duration $t_{exp}$=MED, the fabric cools within a corresponding duration and releases heat storage to skin. In this case, skin just reaches a second-degree burn. A cooling duration corresponding to this is defined as a source safe cooling duration.

(3) When a safe thermal exposure duration $t_{exp}$≥PED, skin reaches a second-degree burn even if heat release of skin of the fabric is not considered. In this case, there is no safe cooling duration $t_{co1}$, that is, $t_{co1}$=0. The duration is defined as a first safe cooling duration.

(4) When MED<a safe thermal exposure duration $t_{exp}$<PED, critical values of a plurality of safe cooling durations $t_{co1}$ need to be obtained according to the following process. The plurality of durations is defined as a plurality of third safe cooling durations:

First, at least three thermal exposure durations $t_{trial1}$, $t_{trial2}$, and $t_{trial3}$ are set and all satisfy MED<$t_{trial}$<PED. According to Substep 2-1 and Substep 2-2, heat fluxes of the sensor of the fabric when the thermal exposure durations $t_{trial1}$, $t_{trial2}$, and $t_{trial3}$ are all 60 seconds are separately obtained.

Total durations required for skin burns corresponding to $t_{trial1}$, $t_{trial2}$, and $t_{trial3}$ are separately calculated. The heat flux obtained by the sensor within the thermal exposure duration $t_{trial}$ and the heat flux obtained by the sensor in the cooling stage are used as boundary conditions in the skin heat transfer model to predict the temperature fields at the depths inside skin according to Formula 1. Then a skin burn is predicted by using the Henriques burn integral model in Formula 2, and a duration when a skin burn threshold $\Omega$ in a prediction model is equal to 1.0 is calculated. The durations are total durations $t_{total1}$, $t_{total2}$, and $t_{total}$ required for skin to reach a second-degree burn, and a third safe cooling duration $t_{co1}$=$t_{total}$-$t_{trial}$.

Step 4: Form a wearing safe duration area. The wearing safe duration area includes information about a safe thermal exposure duration and a safe cooling duration. The persistent thermal exposure duration, the minimum thermal exposure duration, and the plurality of safe thermal exposure durations separately obtained in the foregoing three steps are used as x-axis data and the respectively corresponding first safe cooling duration, second safe cooling duration, and the plurality of third safe cooling durations are used as y-axis data, to form a boundary of the wearing safe duration area. A close area formed by the boundary, ax-axis, and a y-axis is the safe duration zone. Results of wearing safe duration areas of test samples of three tested test samples in this embodiment are shown in FIG. 1.

Compared with the conventional indicators PED and MED, a two-dimensional wearing safe duration area provides more comprehensive and richer thermal protection duration information. The thermal protective performance of a fabric under different conditions may be studied by analyzing the safe duration zones of different fabric systems. A fabric B1 with the thickest thermal insulation layer has the largest safe duration zone. However, fabric systems A1 and A2 are sorted differently in thermal protective performance under different conditions. For example, a case O (the thermal exposure duration is 72 seconds, and the cooling duration is 30 seconds) exceeds a safe zone of the fabric A2 but falls within a safe zone of the fabric A1. Under this test condition, the thermal protective performance of the fabric A1 is higher than that of the fabric A2. However, when the test condition is changed to a case P (the thermal exposure duration is 146 seconds, and the cooling duration is 3 seconds), the point falls within the safe zone of the fabric A2, but exceeds the safe zone of the fabric A1. In this case, the thermal protective level of the fabric A1 is lower than that of the fabric system A2. As can be seen, under different test conditions, evaluation results of the thermal protective performance of fabrics vary greatly. A safe duration zone avoids the limitation of a conventional thermal protective performance test indicator. This may make it convenient to compare thermal protective levels of fabrics under different test conditions and can provide an end user such as a firefighter with a relatively clear skin burn prevention strategy. As can be seen from a safe duration zone, information about a thermal exposure duration and cooling duration that need to be controlled to avoid burns can be conveniently observed from the wearing safe duration area.

Although the principle and implementations of the present invention are described by using specific embodiments of the present invention, descriptions of the embodiments are merely intended to help understand the methods and core idea of the present invention. In addition, for a person with ordinary skill in the art, according to the idea of the present invention, changes may be made to the specific implementation and the scope of application. In summary, the content of this specification should not be construed as a limitation to the present invention.

What is claimed is:

1. A method for evaluating a thermal protection duration of a fabric, comprising steps of:

exposing a front surface of a first fabric to a simulated heat source for $t_0$ seconds and continuously acquiring a first heat flux absorbed by a skin simulant sensor on a rear surface of the first fabric within the $t_0$ seconds;

obtaining a persistent thermal exposure duration according to the first heat flux, a human skin heat transfer model, and a burn integral model, wherein the persistent thermal exposure duration represents a maximum duration of allowable persistent thermal exposure of the first fabric for human skin to reach a second-degree burn;

obtaining a first safe cooling duration corresponding to the persistent thermal exposure duration;

exposing a front surface of a second fabric to the simulated heat source for $t_1$ seconds, subsequently removing the second fabric from the simulated heat source to perform cooling, and continuously acquiring a second heat flux absorbed by a skin simulant sensor on a rear surface of the second fabric during the $t_1$ seconds of thermal exposure and a preset duration of the cooling, wherein the second fabric is the same as the first fabric, and $t_1 < t_0$;

obtaining a minimum thermal exposure duration according to the second heat flux, the skin heat transfer model, and the burn integral model, wherein the minimum thermal exposure duration represents a minimum duration of required persistent thermal exposure of the second fabric for human skin to reach a second-degree burn;

obtaining a second safe cooling duration corresponding to the minimum thermal exposure duration;

separately exposing front surfaces of a third fabric to the simulated heat source for $t_{trial}$ seconds, subsequently removing the third fabric from the simulated heat source to perform cooling, continuously acquiring a third heat flux absorbed by skin simulant sensors on rear surfaces of the third fabric during the $t_{trial}$ seconds of thermal exposure and the preset duration of the cooling, wherein the minimum thermal exposure duration<$t_{trial}$<the persistent thermal exposure duration, the third fabric has a different $t_{trial}$, and the third fabric is the same as the first fabric;

obtaining a third safe cooling duration corresponding to a safe thermal exposure duration according to the third heat flux, the skin heat transfer model, and the burn integral model; and obtaining a safe duration curve according to the persistent thermal exposure duration, the first safe cooling duration corresponding to the persistent thermal exposure duration, the minimum thermal exposure duration, the second safe cooling duration corresponding to the minimum thermal exposure duration, the safe thermal exposure duration, and the third safe cooling duration corresponding to the safe thermal exposure duration.

2. The method according to claim 1, wherein a method for acquiring the second heat flux comprises the steps of:

continuously exposing the second fabric to the simulated heat source for the $t_1$ seconds, making the front surface of the second fabric face the simulated heat source, and placing the skin simulation sensor on the rear surface of the second fabric to continuously acquire a heat flux that transfers through the second fabric within the $t_1$ seconds; and after the thermal exposure of the second fabric ends, removing the second fabric from the simulated heat source to perform cooling, continuously applying a pressure of 13.8±0.7 kPa to the front surface of the second fabric to make the rear surface of the second fabric tightly contact the skin simulant sensor to simulate a process in which a fabric is compressed to quickly release stored thermal energy to skin, and continuously acquiring a heat flux from the rear surface of the second fabric by using the skin simulant sensor within 60 seconds after the cooling is started, wherein the heat flux, which is continuously acquired through the second fabric during the thermal exposure and the cooling is the second heat flux.

3. The method according to claim 1, wherein a method for acquiring the third heat flux comprises the steps of:

continuously exposing the third fabric to the simulated heat source for the $t_{trial}$ seconds, making the front surfaces of the third fabric face the simulated heat source, and placing the skin simulant sensors on the rear surfaces of the third fabric to continuously acquire heat that transfers through the third fabric within the $t_{trial}$ seconds; and after the thermal exposure of the third fabric ends, removing the third fabric from the simulated heat source to perform cooling, continuously applying a pressure of 13.8±0.7 kPa to the front surfaces of the third fabric to make the rear surface of the third fabric tightly contact the skin simulant sensors to simulate a process that a fabric is compressed to quickly release stored thermal energy to the skin, and continuously acquiring a heat flux on the rear surfaces of the third fabric by using the skin simulant sensors within 60 seconds after the cooling is started, wherein the heat flux, which is continuously acquired by the third fabric during the thermal exposure and the cooling is the third heat flux.

4. The method according to claim 1, wherein the step of "obtaining a safe duration curve according to the persistent thermal exposure duration, the first safe cooling duration corresponding to the persistent thermal exposure duration, the minimum thermal exposure duration, the second safe cooling duration corresponding to the minimum thermal exposure duration, the safe thermal exposure duration, and the third safe cooling duration corresponding to the safe thermal exposure duration" comprises: obtaining the safe duration curve by using the persistent thermal exposure duration, the minimum thermal exposure duration, and the safe thermal exposure duration as x-coordinate data and using the respective corresponding first safe cooling duration, second safe cooling duration, and the third safe cooling duration as y-coordinate data.

5. The method according to claim 4, wherein a closed area formed by a boundary being the safe duration curve, an x-axis, and a y-axis is defined as a safe duration zone of the fabric.

6. The method according to claim 1, wherein the skin heat transfer model is:

$$\rho c \frac{\partial T(x, t)}{\partial t} = k \frac{\partial^2 T(x, t)}{\partial x^2},$$

where $\rho$, c, and k are respectively a density, a specific heat capacity, and a thermal conductivity of skin, and T(x, t) is a temperature of a skin layer at a depth of x at a moment t.

7. The method according to claim 6, wherein the burn integral model is:

$$\Omega = \int_0^t P \exp\left(\frac{-\Delta E}{RT}\right) dt,$$

wherein $\Omega$ is burn injury parameter and is dimensionless; $\Delta E$ and P are respectively activation energy of skin and a frequency factor; R is a universal gas constant; T is an absolute temperature of skin; t is a duration for which the skin temperature T is greater than 44° C.; and when $\Omega$ is greater than or equal to 1.0, skin reaches a second-degree burn.

8. The method according to claim 7, wherein a method for obtaining the persistent thermal exposure duration and the first safe cooling duration comprises the steps of:
predicting temperature fields at depths inside the skin according to the skin heat transfer model and using the first heat flux as a boundary condition of the skin heat transfer model; and
retrieving a temperature change at an epidermis/dermis interface of the skin from the temperature fields, and calculating, according to the burn integral model, a duration until a human skin second-degree burn threshold $\Omega$ is equal to 1.0, wherein the duration is the persistent thermal exposure duration, and the first safe cooling duration is 0.

9. The method according to claim 7, wherein a method for obtaining the minimum thermal exposure duration and the second safe cooling duration comprises the steps of:
predicting temperature fields at depths inside the skin according to the skin heat transfer model and using the second heat flux as a boundary condition of the skin heat transfer model; and
retrieving a temperature change at an epidermis/dermis interface of the skin from the temperature fields, and calculating, according to the burn integral model, a duration until a human skin second-degree burn threshold $\Omega$ is just equal to 1.0, wherein the duration is a total duration of a required thermal exposure duration and a required cooling duration of the second fabric for the human skin to reach a second-degree burn, the required thermal exposure duration corresponding to the threshold is the minimum thermal exposure duration of the second fabric, and a difference between the total duration and the minimum thermal exposure duration is the second safe cooling duration.

10. The method according to claim 7, wherein a method for obtaining the third safe cooling duration comprises the steps of:
predicting temperature fields at depths inside the skin according to the skin heat transfer model and using the third heat flux as a boundary condition of the skin heat transfer model; and
retrieving a temperature change at an epidermis/dermis interface of the skin from the temperature fields, and calculating, according to the burn integral model, a duration until a human skin second-degree burn threshold $\Omega$ is equal to 1.0, wherein the duration is a total duration of a required thermal exposure duration and a required cooling duration of the third fabric for the human skin to reach a second-degree burn, and a difference between the total duration and corresponding $t_{trial}$ is the third safe cooling duration.

* * * * *